United States Patent [19]

Mizukami et al.

[11] Patent Number: 5,665,703
[45] Date of Patent: Sep. 9, 1997

[54] GE3 COMPOUND

[75] Inventors: Tamio Mizukami; Yasushi Sakai; Tetsuo Yoshida; Tsutomu Agatsuma, all of Machida; Keiko Ochiai, Ebina; Shiro Akinaga, Sunto-gun, all of Japan

[73] Assignee: Kyowa Hakko Kogyo Co., Ltd., Japan

[21] Appl. No.: 567,529

[22] Filed: Dec. 5, 1995

Related U.S. Application Data

[63] Continuation-in-part of PCT/JP95/00627, Mar. 31, 1995.

[30] Foreign Application Priority Data

Apr. 7, 1994 [JP] Japan .................... 6-069760

[51] Int. Cl.$^6$ .................................... C07K 11/02
[52] U.S. Cl. .................... 514/11; 514/9; 530/3; 530/17
[58] Field of Search .................... 530/317; 514/9, 514/11

[56] References Cited

PUBLICATIONS

'The Journal of Antibiotics' "Verucopeptin↑, A New Antitumor Antibiotic Active Against B16 Melanoma" Nishiyama et al pp. 9221–927 Jun. 1993.

'The Journal of Antibiotics' "Structural Studies on New Depsipeptide Antibiotics, Variapeptin and Citropeptin", Nakagawa et al, pp. 477–484 May 1990.

'Agric. Biol. Chem', "A New Depsipept;Ide Antibiotic, Citropeptin" Hayakawa et al, pp. 1007–1011 Apr. 1990.

*Primary Examiner*—Howard E. Schain
*Attorney, Agent, or Firm*—Nixon & Vanderhye

[57] ABSTRACT

A GE3 compound of the formula (I) having antibacterial and antitumor properties:

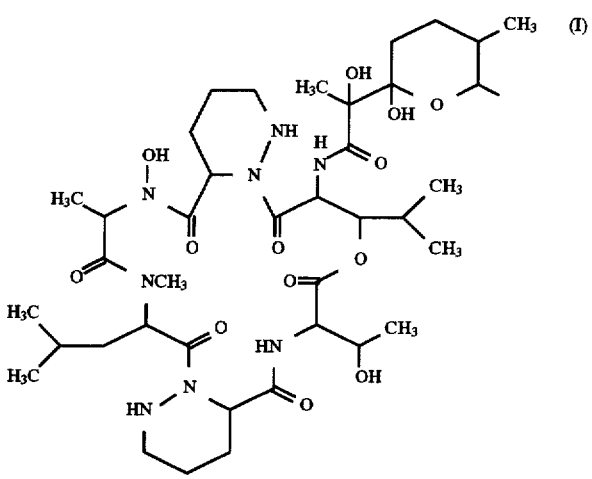

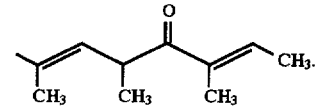

2 Claims, No Drawings

GE3 COMPOUND

This is a continuation-in-Part of PCT application No. PCT/JP95/00627, filed 31 Mar. 1995.

This invention relates to a GE3 compound which has antibacterial and antitumor effects and, therefore, is useful as an antibacterial and antitumor agent.

BACKGROUND OF THE INVENTION

There have been reported compounds such as verucopeptin as hexadepsipeptide-series antitumor antibiotics [Journal of Antibiotics, 46, 921–927 (1993)].

Also known is citropeptin which is represented by the formula (II) and has antitumor properties [Journal of Antibiotics, 3, 477–484 (1990)].

This GE3 compound can be obtained by incubating a microorganism belonging to the genus Streptomyces.

The physicochemical properties of GE3 compound are as follows:

Appearance: white powder.
Melting point: 213°–215° C.
Specific rotation: $[\alpha]_D^{27}$=+111.5° (c=0.08, CHCl$_3$).
Element analysis:
found (%) C: 57.08, H: 7.81, N: 10.76,
calcd. (%) C: 57.52, H: 8.08, N: 10.95 ($C_{49}H_{80}N_8O_{14}\cdot H_2O$).
Mass spectrum: positive ion FAB-MS m/z 987 [M-H$_2$O+H]$^+$ negative ion FAB-MS m/z 1003.5720 [M-H]$^-$(calcd. 1003.5716, $C_{49}H_{79}N_8O_{14}$).
Molecular formula: $C_{49}H_{80}N_8O_{14}$.
UV absorption spectrum: $\lambda_{max}$ (CH$_3$OH): 237 nm (sh).

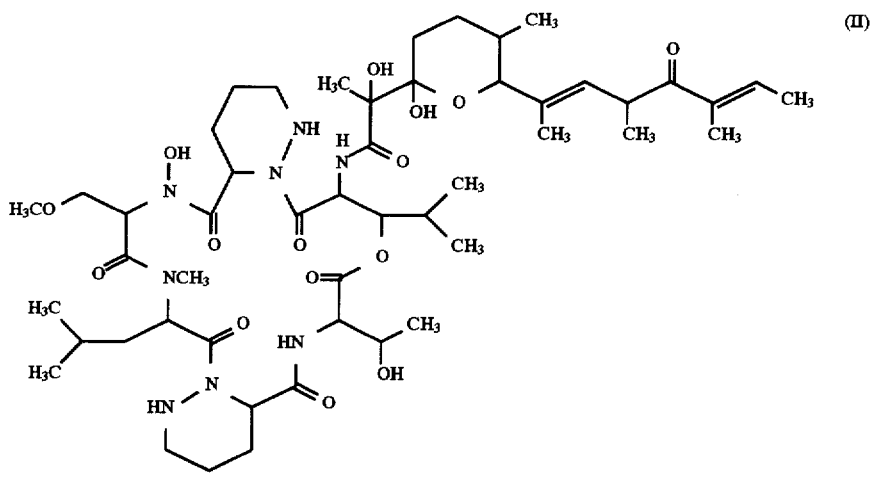

(II)

DISCLOSURE OF THE INVENTION

The present invention provides a GE3 compound which is represented by the formula ( I ) and has antibacterial and antitumor effects.

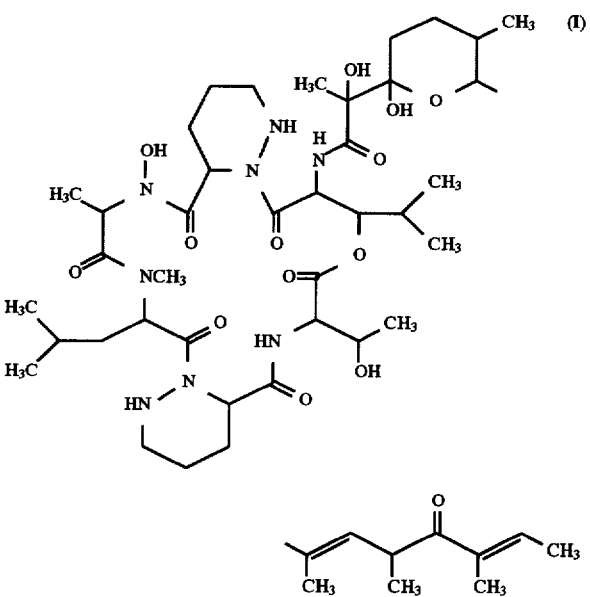

(I)

IR absorption spectrum: $\lambda_{max}$ cm$^{-1}$ (KBr): 3419, 2935, 1734, 1645, 1506, 1315, 1217.

$^1$H-NMR spectrum (CDCl$_3$): δ ppm: 9.88 (br, s, 1 H), 8.24 (d, J=10.7 Hz, 1 H), 6.72 (dq, J=1.3, 7.0 Hz, 1 H), 6.37 (s, 1 H), 6.23 (t, J=7.4 Hz, 1 H), 6.19 (d, J=8.5 Hz, 1 H), 5.58 (dd, J=1.2, 9.1 Hz, 1 H), 5.41 (dd, J=2.3, 10.7 Hz, 1 H), 5.19 (dd, J=1.8, 5.9 Hz, 1 H), 5.15 (q, J=7.1 Hz, 1 H), 4.93 (dd, J=2.7, 10.7 Hz, 1 H), 4.84 (t, J=10.7 Hz, 1 H), 4.80 (q, J=6.5 Hz, 1 H), 4.54 (s, 1 H), 4.53 (d, J=8.5 Hz, 1 H), 4.40 (dd, J=2.0, 12.8 Hz, 1 H), 4.06 (dq, J=9.1, 6.9 Hz, 1 H), 3.96 (d, J=10.3 Hz, 2 H), 3.32 (d, J=12.8 Hz, 1 H), 3.16 (d, J=13.5 Hz, 1 H), 3.01 (s, 3 H), 2.98 (s, 1 H), 2.89 (m, 1 H), 2.63 (m, 1 H), 2.57 (d, J=11.7 Hz, 1 H), 2.28 (d, J=11.7 Hz, 1 H), 1.94 (m, 1 H), 1.85 (d, J=7.0 Hz, 3 H), 1.78 (d, J=1.3 Hz, 3 H), 1.75 (m, 4 H), 1.71 (m, 1 H), 1.65 (m, 2 H), 1.64 (m, 1 H), 1.58 (d, J=1.2 Hz, 3 H), 1.57 (m, 2 H), 1.49 (d, J=7.1 Hz, 3 H), 1.47 (m, 2 H), 1.46 (m, 1 H), 1.44 (m, 1 H), 1.37 (s, 3 H), 1.12 (d, J=6.9 Hz, 3 H), 1.07 (d, J=6.5 Hz, 3 H), 0.96 (d, J=6.4 Hz, 6 H), 0.84 (d, J=6.8 Hz, 3 H), 0.75 (d, J=6.9 Hz, 3 H), 0.72 (d, J=6.6 Hz, 3 H).

$^{13}$C-NMR spectrum (CDCl$_3$): δ ppm: 203.1 (s), 176.6 (s), 173.9 (s), 173.7 (s), 172.3 (s), 170.8 (s), 170.3 (s), 169.6 (s), 137.7 (s), 136.7 (d), 133.1 (s), 129.5 (d), 99.6 (s), 82.2 (d), 78.6 (d), 77.0 (s), 64.9 (d), 56.4 (d), 55.0 (d), 52.4 (d), 51.8 (d), 50.7 (d), 49.7 (d), 47.9 (t), 46.1 (t), 38.5 (d), 36.6 (t), 32.6 (d), 29.7 (q), 29.6 (d), 28.0 (t), 27.3 (t), 25.0 (t), 24.5 (t), 24.2 (t), 22.9 (q), 22.8 (q), 21.5 (t), 21.3 (t), 20.2 (q), 19.4 (q), 19.2 (q), 19.0 (q), 17.7 (q), 15 0 (q), 14.9 (q), 13.5 (q), 12.3 (q), 11.4 (q).

Solubility: soluble in dimethyl sulfoxide (DMSO), methanol, chloroform and acetone but hardly soluble in water.

Color reaction: positive to iodine staining reagent.
Thin layer chromatography: Rf 0.3.
Thin layer: silica gel thin layer (HPTLC plate Art. 15647, manufactured by Merck Co., Inc.).
Developing solvent: methanol:chloroform=2:98 (v/v). After the development, the spot of GE3 can be detected by using the iodine staining reagent.

The biological activities of GE3 compound are as follows.

(A) ANTIBACTERIAL EFFECTS ON VARIOUS BACTERIA

Table 1 shows the minimum inhibitory concentrations (MIC) of the subject GE3 compound on various bacteria. These antibacterial activities were determined by the agar dilution method with the use of a medium (pH 7) comprising 3 g/l of bactotrypton (manufactured by Difco), 3 g/l of meat extract, 1 g/l of yeast extract, 1 g/l of glucose and 16 g/l of agar.

TABLE 1

| Test strain | Minimum inhibitory concentration (µg/ml) |
|---|---|
| *Staphylococcus aureus* ATCC 6538P | 10.4 |
| *Pseudomonas aeruginosa* Bin H No. 1 | 41.6 |
| *Enterococcus faecium* ATCC 10541 | 10.4 |

(B) GROWTH INHIBITION ON HeLa S3 CELLS

Into each well of a 96-well microtiter plate was pipetted 0.1 ml of a $5\times10^4$ cells/ml suspension of HeLa S3 cells (ATCC HTB22) in MEM medium containing 10% of fetal calf serum (manufactured by Nissui, hereinafter referred to as "medium A"). This plate was incubated in a carbon dioxide gas incubator at 37° C. for 20 hours. Then 0.1 ml of the test compound, which was appropriately diluted with the medium A, was added to each well followed by incubation in the carbon dioxide gas incubator at 37° C. for additional 72 hours. After removing the culture supernatant, the residue was washed with physiological saline once and treated with 0.1 ml of methanol for 10 minutes to thereby fix the cells. Next, the cells were stained with 0.1 ml of Giemsa's staining solution [stock solution for Giemsa's staining Merck Art 9204 (manufactured by Merck Co., Inc.): physiological saline=1:10] for 5 minutes. After removing the staining solution, the residue was washed with 0.2 ml of water once. Then the pigment was extracted with 0.2 ml of 0.1N hydrochloric acid and the absorbance was measured at 620 nm with the use of a microplate reader. By comparing the absorbance of the cells treated with the test compound of a known concentration with that of the untreated cells, the 50% inhibitory concentration ($IC_{50}$) of the test compound against the cell growth was calculated. Table 2 shows the results.

TABLE 2

| Compound | $IC_{50}$ (nM) |
|---|---|
| GE3 | 6 |

(C) ANTITUMOR EFFECT ON PSN-1 HUMAN PANCREATIC CARCINOMA-TRANSPLANTED NUDE MOUSE

The antitumor effect on a nude mouse having PSN-1 human pancreatic carcinoma transplanted thereinto was examined in accordance with a method described in literature (Akinaga S. et al., Cancer Res., 51:4888, 1991). Namely, a PSN-1 human pancreatic carcinoma was excised from a mouse for subculture and a tumor section (8 $mm^3$, 2×2×2 mm) was subcutaneously transplanted into the abdomen of a BALB/c-nu/nu mouse (nude mouse) by using a trocar. Eleven days after the transplantation, growth of the tumor was confirmed. Then the test drug was intraperitoneally administered once on the same day.

The antitumor effect was determined in the following manner. The major axis and the minor axis of the tumor are measured with calipers and the tumor volume was calculated in accordance with the formula (Geran RI et al., Cancer Chemother. Rep. Part III, 3:1, 1972): (major axis)×(minor axis)$^2$/2. The antitumor effect is expressed in terms of the ratio (T/C) of the tumor volume (T) of the test group to the tumor volume (C) of the control group to which no drug was administered. Table 3 shows the results.

TABLE 3

| Compound | Dose (mg/kg) | T/C |
|---|---|---|
| GE3 | 2.0 | 0.47 |

Next, a process for producing the compound GE3 will be described.

GE3 can be produced by incubating a microorganism, which belongs to the genus Streptomyces and is capable of producing GE3, in a medium to allow it to produce and accumulate GE3 in the culture medium and collecting GE3 from the culture.

As the microorganism capable of producing GE3, any strain may be employed so long as it belongs to the genus Streptomyces and has ability to produce GE3. Alternatively, use can be made of variants, for example, those obtained by artificially mutagenizing the above-mentioned strains by, for example, UV irradiation, X-ray irradiation or treatment with mutagenic agents and spontaneously mutagenized ones, in the present invention, so long as they are capable of producing GE3. A suitable example of such a microorganism is Streptomyces sp. GE3 strain.

The bacteriological properties of the Streptomyces sp. GE3 strain were as follows.

These properties were determined in accordance with the methods recommended by International Streptomyces Project (ISP) for the determination of the properties of Streptomyces species [E. B. Shirling and D. Gottlieb, Int. J. Syst. Bacteriol., 16, 313–340 (1966)].

A diaminopimelic acid isomer in the hydrolyzate of the whole cells was identified by the method of B. Becker et al. [Appl. Microbiol., 12, 421–423 (1964)].

An optical microscope was used in the morphological observation. In particular, the form of the spore surface was observed under a scanning electron microscope.

Colors are expressed in names described in Color Harmony Manual [Container Corporation of America, 4th ed., (1958)].

1. Morphological properties
  1) Mycelium
     Aerial mycelium formation: yes.
     Aerial mycelium fragmentation and motility: no.
     Substrate mucelium fragmentation and motility: no.
  2) Spore
     Sporulation and spore location: formed on hyphae.
     Sporangium formation and location: no.
     Number of spores linked on sporophore: 10 or more.
     Form of spores linked together: curvaceous or spiral.

Characteristics of spore
  Surface structure: smooth. Form and size: short bacillus, 0.8–1.0×0.9–1.1 μm.
  Motility and flagellum: no.
3) Others
  Chlamydospore: no.
  Synema: no.
  Pseudosporangium: no.
  Mycelium fragmentation: simple branching.

2. Incubation properties

The GE3 strain moderately or vigorously grows in synthetic and natural media commonly employed in the art. The substrate mycelium have a brown color. On some media, it produces a soluble pale brown pigment.

The following data show the growth and color characteristics observed when incubating the GE3 strain on various media at 28° C. for 14 days.

1) Sucrose nitrate agar medium
  Growth: moderate.
  Substrate mycelium color: light olive gray (11/2 ge).
  Aerial mycelium formation and color: poor, white (a)—citron gray (1 ge).
  Soluble pigment: no.
2) Glucose asparagine agar medium
  Growth: moderate.
  Substrate mycelium color: light wheat (2 ea)—butterscotch (31 c).
  Aerial mycelium formation and color: moderate, white (a)—light moss green (lie).
  Soluble pigment: no.
3) Glycerol asparagine agar medium
  Growth: excellent.
  Substrate mycelium color: light olive gray (11/2 ge).
  Aerial mycelium formation and color: vigorous, pale yellow (1 ca)—light citron gray (1 ec).
  Soluble pigment: no.
4) Starch inorganic salt agar medium
  Growth: excellent.
  Substrate mycelium color: light gold (2 ic)—camel (3 ic).
  Aerial mycelium formation and color: vigorous, white (a)—pale yellow (1 ca).
  Soluble pigment: little (pale yellow).
5) Tyrosine agar medium
  Growth: excellent.
  Substrate mycelium color: light ivory (2 ca)—oatmeal (2 ec).
  Aerial mycelium formation and color: vigorous, white (a)—light citron gray (1 ec).
  Soluble pigment: no.
6) Vegetative agar medium
  Growth: moderate.
  Substrate mycelium color: light wheat (2 ea)—light mustard tan (2 ie).
  Aerial mycelium formation and color: vigorous, white (a).
  Soluble pigment: yes (ocher).
7) Yeast malt agar medium
  Growth: excellent.
  Substrate mycelium color: butterscotch (31 c)—light brown (4 ng).
  Aerial mycelium formation and color: vigorous, white (a)—pale lemon yellow (1 ea).
  Soluble pigment: yes (pale ocher).
8) Oatmeal agar medium
  Growth: excellent.
  Substrate mycelium color: light beige (3 ec)—beige (3 ge).
  Aerial mycelium formation and color: vigorous, white (a)—citron gray (1 ge).
  Soluble pigment: little (yellow).

3. Physiological properties

The physiological properties of the GE3 strain are as follows. The growth temperature range is determined after incubating the strain for 10 days, while other data show the results obtained by 2- to 3-week incubation at 28° C.

1) Growth temperature range: 5.0°–37.0° C.
2) Liquefaction of gelatin: no.
3) Hydrolysis of starch: yes.
4) Coagulation and peptonization of skim milk powder: peptonizing.
5) Melanoid pigment formation:
  (i) peptone yeast iron agar medium: no.
  (ii) tyrosine agar medium: no.
6) Utilization of carbon source (basal medium:
  Pridham and Gottlieb agar medium): hereinafter, + will stands for "utilizing", while − will stands for "not utilizing".
  L-Arabinose: −.
  D-Xylose: +.
  D-Glucose: +.
  Sucrose: −.
  Raffinose: −.
  D-Fructose: +.
  L-Rhamnose: +.
  Inositol: −.
  D-Mannitol: +.

4. Chemical classification

Optical isomer of diaminopimelic acid in cell: LL-form.

Based on these results, the GE3 strain chemically classified into the category of the cell wall I type in accordance with the method for the classification of Actinomycetes [M. P. Lechevalier and H. A. Lechevalier, Int. J. Syst. Bacteriol., 20, 435–443 (1970)]. From a morphological viewpoint, furthermore, it is appropriate to regard this strain as belonging to the genus Streptomyces on the basis of the morphological properties thereof (i.e., the formation of spore chains on aerial mycelium, etc.).

Based on these results, this strain has been named Streptomyces sp. GE3 and deposited at National Institute of Bioscience and Human-Technology, Agency of Industrial Science and Technology since Mar. 25, 1994 under the accession number FER BP-4620 in accordance with Budapest Treaty.

The microorganism capable of producing the GE3 compound of the present invention may be incubated by a conventional method for incubating Actinomycetes. As the medium, either a synthetic medium or a natural one may be used so long as it contains appropriate carbon sources, nitrogen sources and inorganic substances, which can be utilized by the microorganism, and growth and production promoters required for the incubation.

Examples of the carbon sources include glucose, starch, dextrin, mannose, fructose, sucrose, lactose, xylose, arabinose, mannitol and molasses. Any one of these substances or a combination thereof may be used. Hydrocarbons, alcohols and organic acids may also be used depending on the assimilability of the microorganism.

Examples of the nitrogen sources include ammonium chloride, ammonium nitrate, ammonium sulfate, sodium nitrate, urea, peptone, meat extract, yeast extract, dry yeast, corn steep liquor, soybean meal and casamino acids. Any one of these substances or a combination thereof may be used.

In addition, the medium may contain inorganic salts such as sodium chloride, potassium chloride, magnesium sulfate, calcium carbonate, potassium dihydrogen phosphate, ferrous sulfate, calcium chloride, manganese sulfate, zinc sulfate and copper sulfate, if needed. Furthermore, trace components capable of promoting the growth of the microorganism or the production of GE3 may be optionally added thereto.

As the incubation method, liquid culture is preferable and submerged spinner culture is more preferable. The incubation is performed at a temperature of from 16° to 37° C., preferably from 25° to 32° C., at pH 4 to 10, preferably pH 6 to 8. In general, the incubation is completed within 1 to 7 days and thus GE3 is accumulated in the culture medium and the cells. The pH value of the medium is regulated with the use of aqueous ammonia, an ammonium carbonate solution, etc. When the amount of the product in the culture attains the maximum level, the incubation is ceased.

The GE3 thus accumulated in the culture may be isolated and purified in accordance with the methods commonly employed for the isolation and purification of a microbial metabolite from a culture.

For example, the culture is divided into the culture filtrate and the cells by filtration. Then the cells are extracted with, for example, chloroform or acetone. Next, the extract is combined with the culture filtrate and passed through a column packed with a polystyrene adsorbent, for example, Diaion HP20 (manufactured by Mitsubishi Chemical Industries, Ltd.) by which the active component is adsorbed. After eluting with, for example, ethyl acetate or acetone, the eluate is concentrated and subjected to, for example, silica gel column chromatography or high performance liquid chromatography to thereby give GE3. During the incubation, isolation and purification steps, GE3 can be detected by effecting silica gel thin layer chromatography followed by the reaction with an iodine staining reagent.

The GE3 compound obtained by the present invention is useful as an antibacterial and antitumor agent. It may be administered either as such or in various dosage forms. When the GE3 compound is administered by injection, for example, it may be dissolved in a pharmaceutically acceptable diluent commonly employed in the art such as physiological saline, glucose injection, lactose injection or mannitol injection. Alternatively, it may be processed into a lyophilized injection or a powdered injection comprising a mixture of GE3 with sodium chloride in accordance with suitable pharmaceutical practices such as those of the Pharmacopoeia Japan. The injection formulation may also contain adjuvants such as polyethylene glycol or HCO-60 (surfactant, manufactured by Nikko Chemical), or carriers such as ethanol and/or liposomes or cyclodextrin. Although these injections are usually intravenously administered, intraarterial, intraperitoneal or intrathoracic injection may be used.

It is also possible to mix the GE3 compound with appropriate pharmaceutically acceptable carriers and diluents such as fillers, disintegrators, binders or lubricants in a conventional manner to thereby formulate into tablets, granules, powders or syrups for oral administration. The GE3 compound together with carriers commonly employed in the art may be molded into suppositories for rectal administration.

The dose varies depending on the administration method, the type of the GE3 compound, the age and condition of the patient, etc. Also, the administration method/frequency may be varied depending on the conditions, dose, etc. For example, it may be administered at intervals of 1 to 3 weeks in a dose ranging from 0.06 to 6 mg/kg.

BEST MODE FOR CARRYING OUT THE INVENTION

EXAMPLE 1

Streptomyces sp. GE3 strain (FERM BP-4620) was used as an inoculum.

This strain was inoculated into 300 ml of a seed medium (pH 7.2 before sterilization), which was composed of 5 g/l of bactotrypton (manufactured by Difco), 5 g/l of yeast extract, 3 g/l of meat extract, 10 g/l of soluble starch, 10 g/l of glucose and 0.5 g/l of magnesium phosphate, in a 2 L Erlenmeyer flask and incubated under shaking at 200 rpm at 30° C. for 48 hours. The seed culture thus obtained was transferred into 18 L of a fermentation medium of the following composition in a 30 L jar fermentor at a ratio of 5% by volume and incubated therein under aeration/agitation (250 rpm, airflow rate: 18 L/min) at 28° C.

Composition of fermentation medium: 50 g/l of soluble starch, 15 g/l of dry yeast, 0.5 g/l of $KH_2PO_4$, 0.5 g/l of $MgSO_4 \cdot 7H_2O$, 0.5 g/l of magnesium phosphate (pH 7.0 before sterilization, adjusted with NaOH).

Incubation was continued for 96 hours without particularly regulating the pH value of the medium. Then the culture was divided into the culture filtrate and the cells by filtration. The cells were extracted with acetone. After concentrating the extract, water was added thereto. Then it was combined with the culture filtrate and passed through a column packed with a polystyrene adsorbent Diaion HP20 (manufactured by Mitsubishi Chemical Industries, Ltd.) on which the active component was adsorbed. After eluting the impurities with deionized water, 33% methanol and 66% methanol, the active substance was eluted with 100% methanol. The methanol fraction was concentrated, applied to a silica gel column (Wakogel C-200, manufactured by Wako Pure Chemical Industries), and developed and fractionated with a solvent mixture of chloroform/methanol (0.5% stepwise method). The active fraction thus eluted was concentrated, applied to an ODS column (ODS-AM 120-230/70, manufactured by YMC), and developed and fractionated with a solvent mixture of methanol/water [4:1 (v/v)]. The active fraction thus eluted was concentrated and subjected to high performance liquid chromatography (HPLC) under the conditions as specified below. After developing with a solvent mixture of methanol/water [4:1 (v/v)], a fraction taken up with the use of the end absorption as an indication was lyophilized. Thus 25 mg of the GE3 compound was obtained as a white powder.

HPLC conditions

Column: ODS 120A S-5 (SH363-5) (manufactured by YMC).

Eluent: 80% methanol.

Flow rate: 20 ml/min.

Detection: 230 nm.

Retention time: 52.5 min.

We claim:

1. GE3 compound represented by the formula (I):

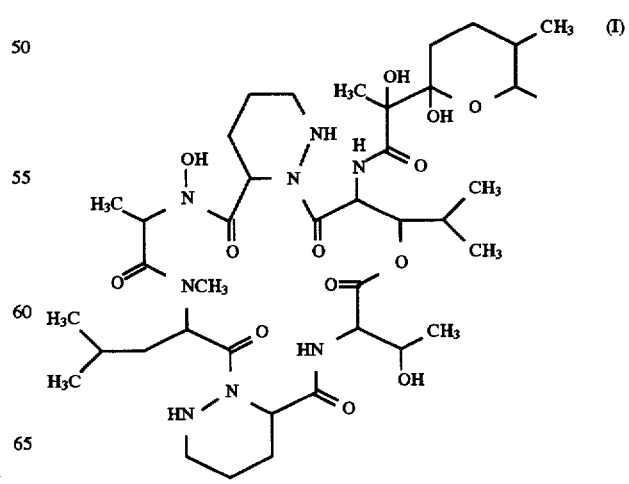

-continued
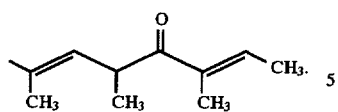
5
2. A pharmaceutical composition comprising the compound of claim 1 and a pharmaceutically acceptable carrier or diluent.
* * * * *